United States Patent
Ding et al.

(10) Patent No.: US 7,828,956 B2
(45) Date of Patent: Nov. 9, 2010

(54) METHOD FOR MEASURING CONCENTRATIONS OF GAS MOIETIES IN A GAS MIXTURE

(75) Inventors: Yi Ding, Canton, MI (US); Richard Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 1109 days.

(21) Appl. No.: 11/275,485

(22) Filed: Jan. 9, 2006

(65) Prior Publication Data

US 2008/0149499 A1     Jun. 26, 2008

(51) Int. Cl.
    *G01N 27/407*     (2006.01)
(52) U.S. Cl. ............... 205/781; 205/784.5; 204/425; 204/424
(58) Field of Classification Search ......... 204/424–429, 204/431; 205/783.5, 775, 778, 780.5, 781, 205/782, 782.5, 783, 784, 784.5, 785, 785.5, 205/793.5; 73/1.01, 1.02, 1.03, 1.16, 1.06, 73/23.2–23.33, 114.01, 114.69–114.76
See application file for complete search history.

(56) References Cited

U.S. PATENT DOCUMENTS

| | | | | |
|---|---|---|---|---|
| 4,542,640 A | * | 9/1985 | Clifford | ............ 73/31.06 |
| 4,847,783 A | * | 7/1989 | Grace et al. | ............ 702/24 |
| 5,831,145 A | * | 11/1998 | Logothetis et al. | ............ 73/23.2 |
| 6,551,497 B1 | * | 4/2003 | Gao et al. | ............ 205/781 |
| 6,764,591 B1 | * | 7/2004 | Dutta et al. | ............ 205/781 |
| 6,805,782 B2 | | 10/2004 | Tanaka et al. | |
| 2003/0209434 A1 | | 11/2003 | Martin et al. | |
| 2004/0138825 A1 | | 7/2004 | Kawase et al. | |
| 2004/0149579 A1 | | 8/2004 | Palmer et al. | |
| 2005/0016871 A1 | * | 1/2005 | Compton et al. | ............ 205/782 |

OTHER PUBLICATIONS

Fraden (Handbook of Modern Sensors, Second Edition, Springer, Section 2.1, pp. 10-12, 1996.*

* cited by examiner

*Primary Examiner*—Alexa D Neckel
*Assistant Examiner*—Jennifer Dieterle
(74) *Attorney, Agent, or Firm*—Damian Porcari; Brooks Kushman P.C.

(57) ABSTRACT

In at least one embodiment, a method is described for measuring concentrations of gas moieties in a gas mixture. A mixed-potential gas sensor is exposed to a gas mixture in order to obtain a first and a second mixed-potential gas sensor output responses. The first output response and a second output response are deconvoluted to measure a first analyte gas concentration and a second analyte gas concentration. Some of the output responses may be used as inputs to a control system.

12 Claims, 2 Drawing Sheets

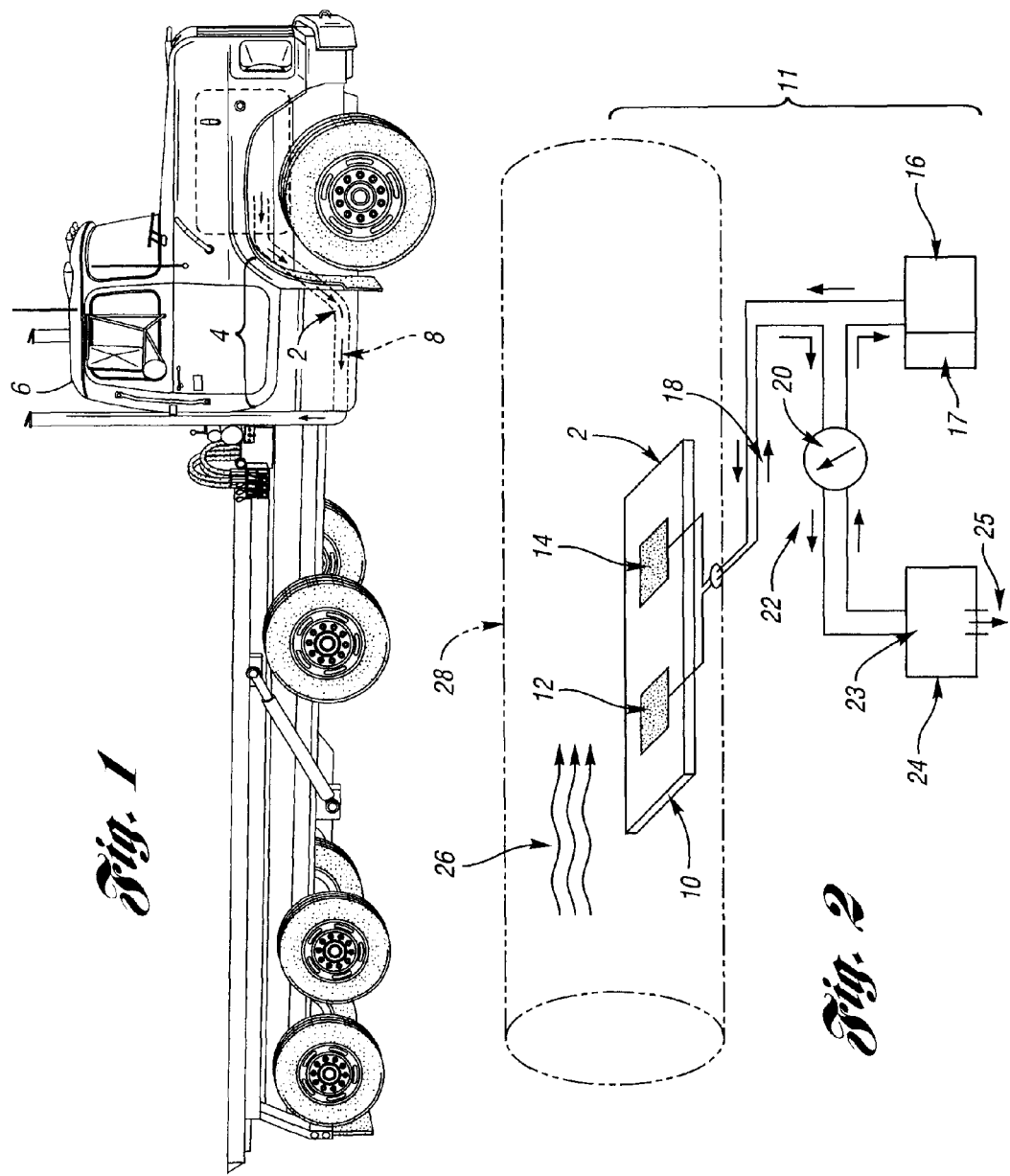

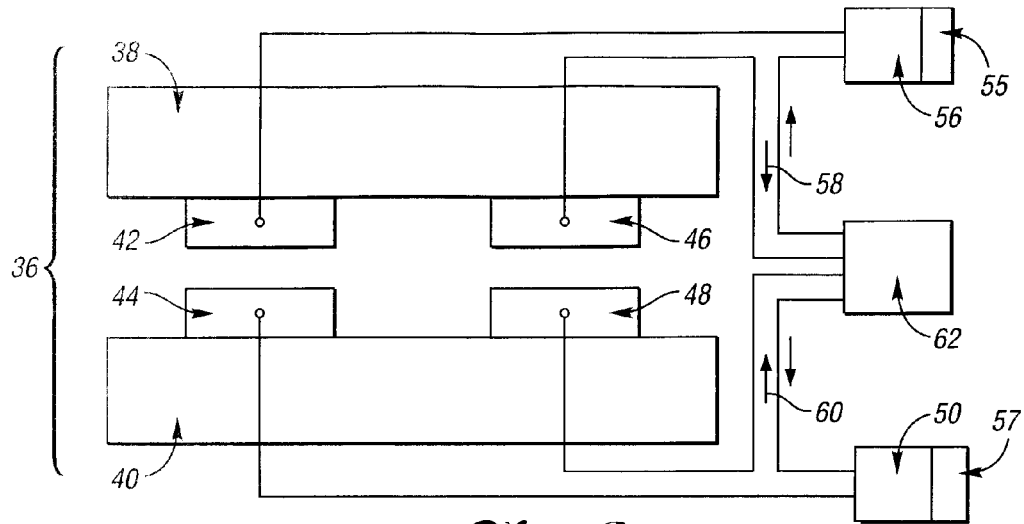
Fig. 3
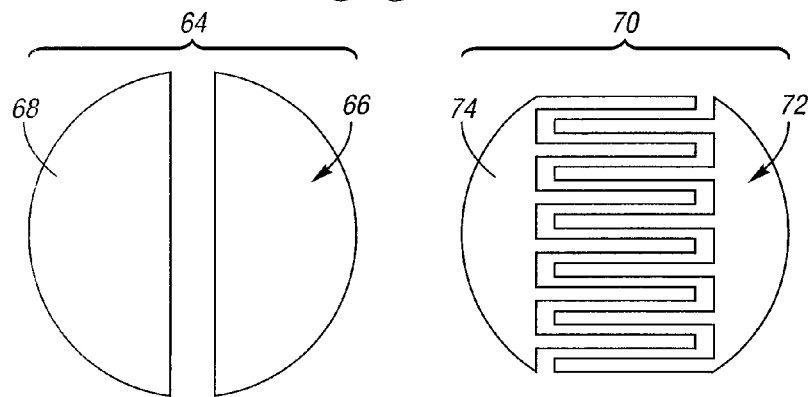
Fig. 4a
Fig. 4b
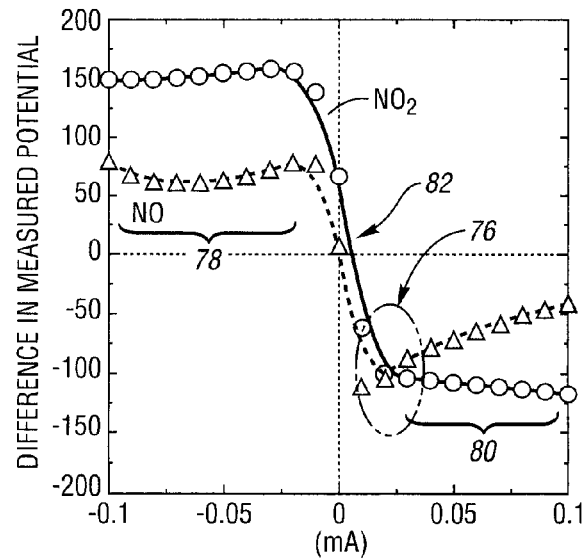
Fig. 5

METHOD FOR MEASURING CONCENTRATIONS OF GAS MOIETIES IN A GAS MIXTURE

BACKGROUND OF THE INVENTION

1. Field of the Invention

One aspect of the present invention relates to a method for measuring concentrations of gas moieties in a gas mixture.

2. Background Art

Many control systems rely on sensors to provide useful information regarding a concentration of a gas moiety in a gas mixture. Certain gas moieties may be suitable for determination of their concentrations by an electrochemical measurement. The electrochemical measurement may be acquired relatively simply and inexpensively by use of a gas sensor. However, some gas sensors may provide relatively slow output response signals to electrochemical changes in the gas mixture, or may exhibit a relative lack of sensitivity for a desired gas moiety. For example, the sensitivity may be diminished if the electrochemical changes of two chemical moieties are of opposite electrochemical sign. In certain cases, the opposite electrochemical signs may cancel each other, yielding a relatively low intensity net signal. In another example, the electrochemical response may be either augmented or diminished by an interfering gas moiety. For example, water vapor or oxygen may interfere with certain gas sensors.

Some sensors previously used methods focused on eliminating the interfering gas moiety. Examples of these methods include tuning the bias to be selective to only one analyte gas moiety; using catalysts to selectively react with the interfering gas moiety in order to yield a non-interfering gas moiety; as well as using an upstream filter or an electrochemical pump to physically remove the interfering gas moiety. Extra steps such as these may be incapable of removing all of the interfering gas moiety, and/or may modify the concentrations of the analyte gas moiety. In general, these methods add unacceptable costs to the method for measuring the concentration of the analyte gas moiety in the gas mixture.

In light of the foregoing, what is needed is a relatively inexpensive, but a relatively sensitive, method for measuring the concentration of the analyte gas moiety in the gas mixture. In addition, the method should be relatively insensitive to interfering gas moieties in the gas mixture without having to be selective for only one gas moiety.

SUMMARY OF THE INVENTION

In at least one embodiment, a mixed-potential gas sensor is exposed to a gas mixture in order to obtain a first output response and a second output response. The first output response and the second output response are deconvoluted to measure a first analyte gas concentration and a second analyte gas concentration. One or more of the output responses or the analyte gas concentrations may be used as an input signal for a control system.

In another embodiment, a method is provided for forming a gas sensor measurement system for measuring concentrations of gas moieties in a gas mixture. The method for forming the gas sensor measurement system may include electrically connecting a circuit having a cathode, an anode, a conductive substrate, and a power supply having a bias controller. The circuit is electrically connected to a signal deconvoluting device which may include a computer-readable instruction set solving a simultaneous equation system.

In another embodiment, a mixed-potential gas sensor for measuring at least one gas moiety in a gas mixture is provided which may include a first electrode; a second electrode; a solid electrolyte, positioned in electrical contact with the first and second electrodes; a power supply; an electrical output measurement device; and a calculation logic circuit. The power supply electrically connects to the first electrode and the electrical output measurement device. The electrical output measurement device electrically connects to the second electrode and the calculation logic circuit.

BRIEF DESCRIPTION OF THE DRAWINGS

FIG. 1 shows an example of the application of the present invention on a vehicle;

FIG. 2 shows an embodiment of a mixed-potential gas sensor measurement system of the present invention;

FIG. 3 shows an embodiment of a mixed-potential gas sensor of the present invention which is usable with the system illustrated in FIG. 2;

FIGS. 4a and 4b show embodiments of a component usable with the mixed-potential gas sensor illustrated in FIG. 3; and FIG. 5 shows certain results of a potentiometric experiment example employing certain embodiments of the present invention.

DETAILED DESCRIPTION OF THE PREFERRED EMBODIMENT(S)

Reference will now be made in detail to compositions, embodiments, and methods of the present invention known to the inventors. However, it should be understood that disclosed embodiments are merely exemplary of the present invention which may be embodied in various and alternative forms. Therefore, specific details disclosed herein are not to be interpreted as limiting, rather merely as representative bases for teaching one skilled in the art to variously employ the present invention.

Except where expressly indicated, all numerical quantities in this description indicating amounts of material or conditions of reaction and/or use are to be understood as modified by the word "about" in describing the broadest scope of the present invention. Practice within the numerical limits stated is generally preferred.

The description of a group or class of materials as suitable for a given purpose in connection with the present invention implies that mixtures of any two or more of the members of the group or class are suitable. Description of constituents in chemical terms refers to the constituents at the time of addition to any combination specified in the description, and does not necessarily preclude chemical interactions among constituents of the mixture once mixed. The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

Referring to FIG. 1, a vehicle such as a truck 6 is shown. The truck 6 has an emissions system 4 with an emissions stream 8. In at least one embodiment, a mixed-potential gas sensor 2 is located within the emissions system 4 in contact with the emissions stream 8.

Referring to FIG. 2, an embodiment of the mixed-potential gas sensor 2 is shown, which forms part of a circuit 11. The gas sensor 2 is shown in FIG. 2 to be positioned within a housing 28. In this embodiment, the housing 28 may be a portion of the emissions system 4. Inside the housing 28, is a gas mixture 26 from the emissions stream 8. The gas mixture 26 is exposed to the mixed-potential gas sensor 2. The mixed-potential gas sensor 2 illustrated in FIG. 2 includes a conductive substrate 10, with a cathode 12, and an anode 14, each of which is electrically connected to the substrate 10. The cathode 12 and the anode 14 are electrically connected, possibly indirectly, to a power supply 17 with a bias controller 16 that regulates a bias. The mixed potential gas sensor 2 can provide an output response 18 when in use. In the illustrated embodiment, the output response 18 is measured by an electrical output measurement device 20. In this embodiment, the electrical output measurement device 20 can provide a response input signal 22 to the calculation logic circuit 24 which has a signal input port 23 and an output port 25.

In an embodiment of the present invention, the mixed-potential gas sensor 2 is exposed to the gas mixture 26. Some non-limiting examples of the gas mixture 26 may be a relatively simple system containing gas moieties having different electromotive forces, such as both nitrogen dioxide ($NO_2$) and nitric oxide (NO); hydrocarbons and carbon monoxide; oxides of sulfur; and oxygenated hydrocarbons. The gas mixture 26 may also be relatively more complex, having a relatively larger number of gas moieties and/or analyte gases. Non-limiting examples from where such complex gas mixtures may emit include the gas mixture from an internal combustion engine, a diesel engine, a natural gas burner, a coal-fired source, an explosive device, and a fuel cell.

The relatively wide range of types of gas mixtures 26 possible may make it desirable to tune the gas sensor 2 to perform more optimally under specific conditions. Non-limiting examples of such specific conditions where tuning may be desirable may include a range of temperatures observed in diesel engine emissions systems or a reduction of cross-sensitivities to other gas moieties in the gas mixture 26, for example, water vapor or oxygen. In an aspect of this embodiment, the tuning of the sensor 2 may be accomplished by proper selection of the bias applied to the circuit 11.

In certain embodiments of the present invention, the circuit 11 may be used to obtain an output response from the gas sensor 2 using a potentiometric analysis. The potentiometric analysis may include a first potential bias of a voltage applied to the circuit 11 by the power supply 17. A resulting first output response may be measured by the electrical output measurement device 20, which, in at least one embodiment, may be an ammeter, and which may measure the quantity of a first current passing through the circuit 11. A second gas sensor output response may be obtained by applying a second potential bias to the circuit 11 and measuring a second current.

In certain embodiments of the present invention, the circuit 11 may be used to obtain the first output response using an amperometric analysis. The amperometric analysis may include a first current bias that may be applied to the circuit 11 by the power supply 17. The resulting first output response may be measured by the electrical output measurement device 20, which, in at least one embodiment, may be a voltmeter, and which may measure the quantity of a first potential passing through the circuit 11. The second gas sensor output response may be obtained by applying a second current bias and measuring a second potential.

Selection of operating parameters of the circuit 11 may reflect a desire to have one of the gas moieties in the gas mixture 26 undergo a chemical reaction at a specific electrode. As a non-limiting example, a first analyte gas moiety may undergo reduction at the cathode while a second analyte gas moiety undergoes oxidation at the anode. Non-limiting examples of the selections of operating parameters may include (a) differing the magnitudes of the first bias and the second bias, while applying the first bias and the second bias sequentially to a first cathode and a first anode formed of a first material; (b) applying the first bias and the second bias at identical magnitudes sequentially to the first cathode formed of the first material and the first anode formed of a second material; (c) simultaneously applying the first bias at a first magnitude to the first cathode and the first anode and applying the second bias having a second magnitude to a second cathode and a second anode, all formed of the first material; or (d) combinations thereof. The number of analyte gas moieties that can be simultaneously measured using certain embodiments of the present invention with an array of cathodes and anodes may be equal to or less than the number of cathodes comprising the array.

In certain embodiments of the present invention, the first and second biases are regulated by the bias controller 16 (FIG. 2), 50 (FIG. 3), or 56. Non-limiting examples of the bias controller may include a rheostat, a resistor, a transistor, a voltage divider, or combinations thereof.

In certain embodiments of the present invention, IC the first and the second gas sensor output responses may be deconvoluted mathematically to yield concentrations of the first analyte gas moiety and the second analyte gas moiety in the gas mixture 26 (FIG. 2). The concentrations of the two gas moieties may be calculated by solving for individual electrical contributions from the gas moieties. The first and second gas sensor output responses may be input signals 22 to the calculation logic circuit 24. Non-limiting forms by which the input signals may be used may include in native form, in electronically sampled condition, in statistically sampled condition, or in conditions manipulated by various means. Non-limiting examples of the manipulation means include the voltage divider, a capacitor, an amplifier, a converter to digital format, a mathematical model, a mathematical algorithm, and a means to convert to other field forms. Non-limiting examples of the field forms may include an optical signal, such as a light pulse; a magnetic field; a mechanical solenoid; a piezoelectric signal; a Zener diode discharge; a capacitive charge; or an acoustical signal such as a sound.

In certain embodiments of the present invention, the solution for individual concentrations of the first and second analyte gases may be accomplished by solving the matrix for n-number of gases in the gas mixture 26. The mathematical deconvolution may include solving the matrix equation $$A = B^{-1} \cdot G$$

where A is a vector of the analyte gas concentrations of the gas moieties in the gas mixture 26, B is the matrix of all transfer functions of electromotive force for reduction potentials of the gas moieties in the gas mixture 26 at all of the biases selected, and G is a vector of mixed-potential gas sensor output responses at all of the biases. The number of biases used must be at least equivalent in number to the number of the gas moieties whose analyses are sought.

In certain embodiments, a non-limiting example of the solution of the matrix equation for a relatively simple gas mixture having the first and the second analyte gas may be reduced to solving the corresponding simultaneous equation system such as $$M = CX + C'Y + C''$$

$$N = DX + D'Y + D''$$

where M is the first mixed-potential gas sensor output response, N is the second mixed-potential gas sensor output response, C is a first transfer function of an electromotive force for the first analyte gas moiety having a first reduction potential at the first bias, and C' is a second transfer function of the electromotive force for the second analyte gas moiety having a second reduction potential at the first bias, D is a first transfer function of a electromotive force for the first analyte gas moiety having the first reduction potential at the second bias, D" is a second transfer function of the electromotive force for the second analyte gas moiety having the second reduction potential at the second bias, X is the concentration of the first analyte gas moiety, Y is the concentration of the second analyte gas moiety, C" is a first constant and D" is a second constant, both of which are associated with aspects of the circuit which may include a choice of sensor materials and the circuit set-up.

A method to derive the transfer functions involves a series of experiments measuring the output response at the applied bias while incrementally increasing the concentration of desired analyte gas moiety in known quantities, thereby creating a calibration curve. This calibration curve experiment may be repeated at additional biases of interest, or using different combinations of electrodes at the same bias, until sufficient data are collected to be able to solve the simultaneous equation system for the transfer function coefficients for all of the gas moieties to be measured.

For a simple system with two analyte gases of interest, the transfer function coefficients may be calculated using the simultaneous equation system, as follows:

$$S = pU + qV + r$$

$$S' = p'U + q'V + r'$$

where S is a measured voltage in both experiments, U is a known concentration of the first analyte gas, V is a known concentration of the second analyte gas, and p, q, and r are transfer function coefficients.

In another embodiment of the present invention, the solution of the matrix, the vector, or the simultaneous equation system may be accomplished by any mathematically-appropriate computational means. Non-limiting examples of these computational means may include a computer-readable device embedded with an instruction set including a software algorithm, a simultaneous equation system solution calculation logic circuit, the signal deconvoluting device, or a computer-readable instruction set that may include a look-up table representing a portion of a response surface. The solution yields the measured concentrations of the analyte gases.

In another aspect of certain embodiments of the present invention, some of the measured concentrations of the analyte gases may be used as the input signal to a control system. Some non-limiting examples of the control system include a feedback loop, a feedforward loop, a monitoring system, a mathematical control model, a mathematical control algorithm, a control system for an emissions remediation system, or combinations thereof. Another non-limiting example is a monitoring control system which monitors one or more analyte gas concentrations. The monitoring control system, in a non-limiting example, may signal exceeding a pre-set limit, trigger another electronic device, or activate a warning device.

Referring to FIG. 3, another embodiment of the present invention is illustrated. In this embodiment, an array of mixed-potential gas sensors 36, is shown. In this embodiment, the sensor 36 has a first conductive substrate 38 and a second conductive substrate 40. In this embodiment a first cathode 42 and a first anode 46 are electrically connected to the first conductive substrate 38 and to a first power supply 55 having a first bias controller 56 which provides a first bias. A second cathode 44 and a second anode 48 are electrically connected to a second conductive substrate 40 and to a second power supply 57 having a second bias controller 50 which provides a second bias. The first output response 58 and the second output response 60 are measured by the electrical output measurement device, such as a scanning electrical output measurement device 62.

In another embodiment of the present invention, the electrodes 12 (FIG. 2), 14, 42 (FIG. 3), 44, 46, 48 in the mixed-potential sensor may function as either cathodes or anodes depending upon the direction of the flow of current as set by the power supply or the bias controller, and/or by the bias level selected. Non-limiting examples of the electrodes are a noble metal member and an oxide member. Non-limiting examples of the noble metal member may comprise noble metals such as platinum or gold. A non-limiting example of the oxide member may comprise a mixed oxide. The mixed oxide may comprise the oxide of a metal typically having multiple valence states of the metal. A non-limiting example of the metal may include a transition metal such as iron, cobalt, and/or chromium. In addition, certain mixed oxides may include a coordinated metal which typically has only one valence state such as a lanthanide metal, an alkali earth metal, or a second transition metal. Non-limiting examples of the mixed oxide include $La_{1-x} Sr_x CrO_3$ (LSC), $La_{1-x} Sr_x CrO_3$ with Gadolinium Carbide, $La_{0.85} Ba_{0.15} CrO_3$, $La_{0.75} Sr_{0.25} Mn_{0.5} Cr_{0.5} O_3$, $La_{0.8} Ca_{0.21} CrO_3$, $CuCr_2O_4$, $La_{0.4} Sr_{0.2} CoO_4$, $NiCr_2O_4$, $La_{0.8} Sr_{0.2} FeO_3$, and $La_{0.6} Sr_{0.4} Fe_{0.8} Co_{0.2} O_3$.

In another aspect of the present invention, construction of the electrodes may include many different arrangements. Non-limiting reasons for differing the arrangements may include efforts to maximize electrode surface area, to facilitate design, and/or to minimize the solid electrolyte area between the cathode 12 and the anode 14. Non-limiting examples on the arrangement include a flat plate design, a multilayered design, a semicircular design, an interlocked design, an interdigitated design or combinations thereof. The layout of the mixed-potential gas sensor circuit using these electrodes may include designs having several orders of magnitude in physical scale as well as electrical bias magnitude and output signal scale. Non-limiting examples include the mixed-potential gas sensor circuit prepared on a circuit board, prepared by a screen printing method, prepared in a lithographically applied pattern, prepared with an etched semiconductor method, or combinations thereof.

Referring to FIGS. 4a and 4b, non-limiting examples of the arrangements of the electrodes that may be used in the design of the mixed-potential gas sensor are shown. FIG. 4a shows the semicircular electrode design 64 with the platinum (Pt) electrode 66 and the $La_{1-x} Sr_x CrO_3$ (LSC) electrode 68. FIG. 4b shows the interdigitated electrode design 70 with the platinum electrode 72 and the mixed oxide electrode 74.

In another aspect of the present invention, the conductive substrate 10 such as the solid electrolyte may include porous materials that conduct oxide ions and/or protons. Non-limiting examples of the solid electrolyte may include a substrate with a mobile oxygen defect; a multi-vacancy defect cluster; a pyrochloric material, such as a yttria-stabilized zirconia (YSZ), or a cation-doped lanthanide such as a gadolinium-, a magnesium- or a calcium-doped cerium oxide; a nanocrystalline cerium oxide; a low-angle grain boundary titanate, such as an iron-doped strontium titanate; or a modified lanthanum chromate, such as a magnesium-modified (β-site) lanthanum chromate or a chromium-deficient lanthanum chromate. The solid electrolyte member may be formed in various shapes and physical forms. Non-limiting examples of the physical form of the solid electrolyte include a sheet, a tape, a laminate, a cladding, a thin film, or combinations thereof, which could be either mesoporous or macroporous.

EXAMPLE 1

The mixed potential sensor may be constructed using the platinum member in electrical contact with the yttria-stabilized zirconia solid electrolyte. The solid electrolyte is in electrical contact with the oxide member. The co-planar semicircular arrangement of the sensor is used. Depending upon the experiment for the study, the oxide member comprises either a p-type NiO, a p-type $Cr_2O_3$, or an n-type ZnO oxide electrode. The oxide electrode and the Pt noble metal electrode are exposed to the gas mixture 26 containing nitric oxide and nitrogen dioxide. The total $NO_x$ concentration ranges from 20 to 120 parts-per-million by volume ($ppm_v$) $NO_x$. The experiment with the p-type $Cr_2O_3$ oxide member is conducted at 600° C. The other oxide members are tested at 700° C. The voltage measured for nitric oxide and nitrogen dioxide as a function of $NO_x$ concentration varies. The results allow the calculation of the calibration curve for these conditions, which may be used to form the transfer function.

EXAMPLE 2

Referring to FIG. 5, this figure shows the output response of the observed voltage difference measured by the mixed-potential gas sensor using Pt and $NiCr_2O_4$ electrodes in the gas mixture 26. The current bias is swept from −0.1 milliamperes (mA) to 0.1 mA. The gas mixture 26 measured has 450 $ppm_v$ $NO_x$, either as NO or $NO_2$, and 70,000 $ppm_v$ oxygen. In this non-limiting example, a range of current biases in circle 76 is typically used by non-mixed potential sensors. Biases that may be suitable for a mixed potential sensor in this non-limiting example are either greater than +0.025 mA 80 or less than −0.025 mA 78. At the current biases where the measured output response for either of the analyte gas moieties approaches zero 82, the sensitivity may become unacceptable as the magnitude of the output response may be relatively similar to the magnitude of the electronic background noise. A sensor may be operated in a selective mode where chosen biases yield the output response near zero except for one desired gas moiety in order to avoid any interfering gas moieties. The mixed-potential gas sensor may be operated in a selective or a non-selective mode.

EXAMPLE 3

In this example, the mixed potential gas sensor is constructed. The solid electrolyte is produced as a disk by tape casting of the YSZ. The casts are laminated as disks and sintered at 1400° C. for 2 hours in air. The disks are about 16 mm in diameter and 1 mm thick. The platinum electrode is applied to the YSZ substrate by a first screen printing followed by firing at 1100° C. for 0.3 hours in air. The $La_{0.85}Ba_{0.15}CrO_3$ mixed oxide electrode is applied to the YSZ substrate in a second screen printing. The two electrodes are screen-printed in a semi-circular arrangement. The mixed oxide electrode is fired at a relatively lower temperature of 900° C. for 1 hour in air. While not wishing to be limited by any particular theory, the relatively lower firing temperature for the mixed oxide electrode is selected as it may avoid reaction between the lanthanum-containing perovskite structure of the mixed oxide and the YSZ substrate.

While the best mode for carrying out the invention has been described in detail, those familiar with the art to which this invention relates will recognize various alternative designs and embodiments for practicing the invention as defined by the following claims.

What is claimed:

1. A method comprising:
    while exposing a gas mixture to a mixed-potential gas sensor including an anode and a cathode, passing a first and second bias between the anode and the cathode to obtain respectively a first and second response differential between the same anode and the same cathode; and
    deconvoluting the first and second response differentials to determine both first and second analyte gas concentrations.

2. The method of claim 1, further comprising the step of:
    inputting the first and second analyte gas concentrations into a control system.

3. The method of claim 1, wherein the mixed-potential gas sensor further includes an electrolyte, a power source, and an electrical property measurement device.

4. The method of claim 1, wherein the gas mixture includes nitric oxide and nitrogen dioxide.

5. The method of claim 1 further comprising providing a chamber configured to receive the gas mixture, wherein the anode and cathode are disposed within the chamber and in contact with the gas mixture.

6. The method of claim 1, wherein the first and second biases are respectively first and second potentials.

7. The method of claim 6, wherein the first and second response differentials are respectively first and second currents.

8. The method of claim 1, wherein the first and second biases are respectively first and second currents.

9. The method of claim 8, wherein the first and second response differentials are respectively first and second potentials.

10. The method of claim 1, wherein the deconvoluting step includes using a non-transitory computer-readable device having an instruction set for solving a simultaneous equation system.

11. The method of claim 10, wherein the using step includes inputting a matrix of transfer functions for the first analyte gas and the second analyte gas in the gas mixture into the computer-readable device.

12. The method of claim 10, wherein the simultaneous equation system is $$M=CX+C'Y+C''$$

$$N=DX+D'Y+D''$$

where M is the first mixed-potential gas sensor response differential, N is the second mixed-potential gas sensor response differential, C is a first transfer function of an electromotive force for the first analyte gas having a first reduction potential at the first bias, and C' is a second transfer function of the electromotive force for the second analyte gas having a second reduction potential at the first bias, D is the first transfer function of the electromotive force for the first analyte gas having a first reduction potential at the second bias, and D' is the second transfer function of the electromotive force for the second analyte gas having the second reduction potential at the second bias, X is the first analyte gas concentration, Y is the second analyte gas concentration, C" is a first constant and D" is a second constant.

* * * * *